United States Patent
Brin et al.

[11] Patent Number: 5,603,704
[45] Date of Patent: Feb. 18, 1997

[54] MULTI-PURPOSE CURVE

[75] Inventors: David S. Brin; John B. Horrigan, both of West Newbury, Mass.

[73] Assignee: Medtronic, Inc., Minneapolis, Minn.

[21] Appl. No.: 496,943

[22] Filed: Jun. 30, 1995

[51] Int. Cl.⁶ .................................................. A61M 25/00
[52] U.S. Cl. .......................................... 604/281; 604/264
[58] Field of Search .................................... 604/281, 280, 604/284, 264; 128/656, 657, 658, 772

[56] References Cited

U.S. PATENT DOCUMENTS

| | | | |
|---|---|---|---|
| 5,203,776 | 4/1993 | Durfee | 604/264 |
| 5,306,263 | 4/1994 | Voda | 604/281 |
| 5,401,258 | 3/1995 | Voda | 604/281 |
| 5,445,625 | 8/1995 | Voda | 604/281 |
| 5,476,453 | 12/1995 | Mehta | 604/281 |

FOREIGN PATENT DOCUMENTS

| | | | |
|---|---|---|---|
| 9212754 | 8/1992 | WIPO | A61M 25/00 |
| 9321983 | 11/1993 | WIPO | A61M 25/00 |

*Primary Examiner*—John D. Yasko
*Attorney, Agent, or Firm*—Dianne M. Plunkett; Harold R. Patton

[57] ABSTRACT

A catheter adapted for placement within a living anatomy, such as the human coronary arterial system, comprises a proximal portion, a first arcuate portion, a second arcuate portion, and a distal tip. The catheter is shaped so that with the distal tip engaged in the coronary ostium, the ellipsoidal shaped second arcuate portion is in contact with the contralateral wall of the aorta, the catheter thus resisting forces tending to displace the distal tip from the ostium.

8 Claims, 1 Drawing Sheet

MULTI-PURPOSE CURVE

FIELD OF THE INVENTION

The present invention relates to guiding catheters, and more particularly, to a guiding catheter with a curve shape which provides an improvement in support for interventional devices which are delivered through the lumen of the guiding catheter. Such a guiding catheter can be used in PTCA procedures such as balloon angioplasty, angiography, atherectomy, stent implantation procedures, or radiology procedures.

BACKGROUND OF THE INVENTION

One of the therapeutic procedures applicable to the present invention is known as percutaneous transluminal coronary angioplasty (PTCA). This procedure can be used, for example, to reduce arterial build-up of cholesterol fats or atherosclerotic plaque. Typically, a guidewire is steered through the vascular system to the lesion site of therapeutic interest. A dilatation catheter is inserted over the guidewire and is tracked along the guidewire to the lesion where the catheter is inflated to dilate the lesion. A guiding catheter acts as a support conduit for both the guidewire and the dilatation catheter. The shape of the guiding catheter, and particularly the distal shape, strongly influence the ability of the physician to position the tip of the guiding catheter within the target lesion. Further, the distal shape is influential in providing support for the interventional device as the physician attempts to manipulate the device within the vasculature of the patient. Curve shapes which offer improved support are known in the art.

U.S. Pat. No. 5,203,776, issued to Burfee, discloses a catheter for insertion through a main artery ostium which comprises a shaft, an integral profiled portion, and an integral tip portion. The profiled portion comprises a series of bends and straight legs.

U.S. Pat. No. 5,401,258, issued to Voda, discloses a catheter for insertion into an artery of a cardiovascular system including a first straight portion extending from the proximal end of the catheter for a distance greater than the length of the artery and a distal end portion extending from the straight portion and bent in a unique manner to enable the distal end to be precisely located relative to the artery.

OBJECTS OF THE INVENTION

With the advent of new interventional devices such as stents and rotational atherectomy devices came a greater challenge for the performance of the guiding catheter. The bulk of the guiding catheter shapes which are in common usage today were developed in the 1970's for the interventional diagnostic procedure and are ill-suited to the use of the new interventional devices.

Because of the relatively larger diameter and stiffness of the new interventional devices as compared to the conventional devices such as balloons, the guiding catheter shapes must be tailored to the lengths, diameters, and stiffness of these devices so that the devices will move smoothly through the guiding catheter. Also, the shapes must be tailored to the coronary anatomy so that the guiding catheter will provide support for the interventional device as the device is being manipulated through the vasculature to the target lesion. It is critical for purposes of support that the guiding catheter assume a buttressing configuration with the contralateral wall of the coronary aorta and that the distal tip of the guiding catheter orient coaxially with the coronary ostium. To accomplish these criteria, an improved guiding catheter shape was developed.

It is an object of the invention to provide an improved guiding catheter which is shaped to provide improved support and ease of interventional device delivery.

DETAILED DESCRIPTION OF THE PREFERRED EMBODIMENTS

Figure 1:
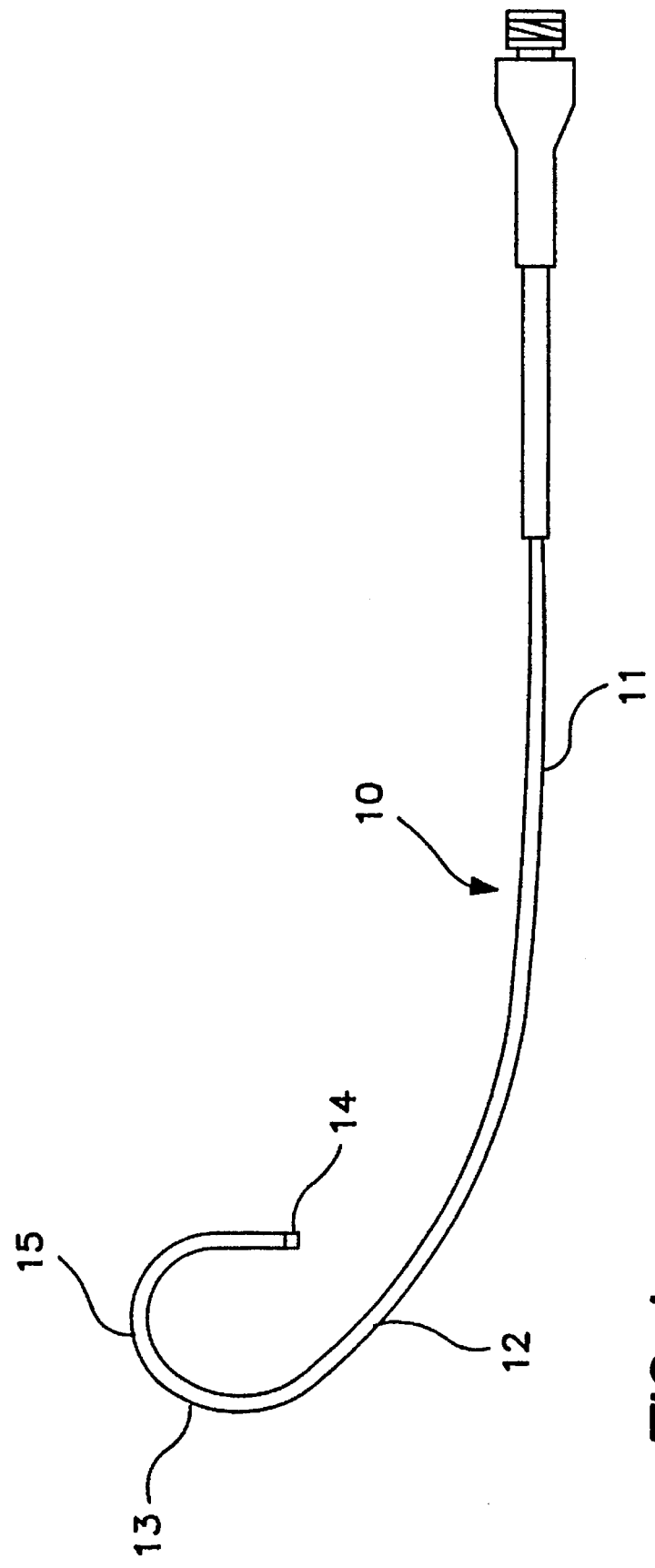
FIG. 1 depicts applicants' improved guiding catheter shape.

Applicants' invention, which is shown generally at 10, encompasses a proximal portion 11, which is substantially straight, of a length of approximately 85 cm, a first arcuate portion 12, extending distally from the proximal portion 11 for a length of approximately 10 cm, a second arcuate portion 13, extending distally from the first arcuate portion 12 for a length of approximately 5 cm, and a distal tip 14, extending distally from the second arcuate portion 13 for a length of approximately 2 mm. The catheter lengths are chosen so that, when the catheter is inserted into the vasculature, the proximal portion extends from the femoral access site to adjacent the aortic arch of the patient, with the first arcuate portion disposed along the contralateral wall of the ascending aorta, and the second arcuate portion spanning the aortic root with the distal tip engaged in the coronary ostium.

The first arcuate portion 12 is a convex curvature with a radius of curvature of approximately 3 to 4 inches adjacent to the proximal portion 11, which blends smoothly to a radius of curvature of 1 to 3 inches distally. The compound radii are sized so that the first arcuate portion 12 can both span the aortic arch proximally and be in intimate contact with the contalateral wall of the ascending aorta distally.

The first arcuate portion 12 blends distally with the second arcuate portion 13, which defines a segment of a generally ellipsoidal shape, the segment being between 135° and 225°. In the preferred embodiment, the segment is preferably 180° and defines two semiaxes. A first semiaxis, which is adjacent to the distal tip 14, has a dimension of 1 to 2 cm; a second semiaxis, at 90 degrees to the first semiaxis, has a dimension of 1 to 3.5 cm. The segment further defines an apex 15, which is adjacent to the second semiaxis. With the distal tip 14 engaged in the coronary ostium, the apex 15 is buttressed against the contralateral wall of the aorta.

The position of the apex 15 relative to the distal tip 14 is such that, when a force tending to displace the distal tip 14 from the ostium acts upon the guiding catheter 10, the line of force acts generally coaxially with the second semiaxis. Because of this coaxiality, the mechanical moment about the apex 15, which is defined as the product of the force times the distance between the line of action of the force and the second semiaxis is zero. With a mechanical moment of zero, there is a significantly reduced tendency of the distal tip 14 to be displaced from the coronary ostium; thus the support of the guiding catheter is enhanced.

In the preferred embodiment, the proximal portion 11, the first arcuate portion 12, the second arcuate portion 13 lie in the same plane. In an alternative embodiment, the second arcuate portion 13 is disposed approximately 5° to 30° out of plane from the first arcuate portion 12.

The preceding embodiments are illustrative of the invention and modifications may be made to these embodiments without departing from the scope and breadth of the invention.

What is claimed is:

1. A catheter adapted for placement within a living anatomy, such as in the human coronary arterial system, the catheter comprising:

a proximal portion, a first arcuate portion, a second arcuate portion, and a distal tip;

the proximal portion being substantially straight;

the first arcuate portion being connected to the proximal portion; the first arcuate portion having a convex curvature, the first arcuate portion having a radius of curvature of 3 to 4 inches adjacent to the proximal portion and 1 to 3 inches distally;

the second arcuate portion being connected between the first arcuate portion and the distal tip, the second arcuate portion blending with the first arcuate portion, the second arcuate portion defining two semiaxes, a first semiaxis being adjacent to the distal tip and having a dimension of 1 to 2 cm; a second semiaxis being adjacent to the first arcuate portion and having a dimension of 1 to 3.5 cm, the second arcuate portion defining a segment of a generally ellipsoidal shape, the segment being between 135° and 225°, the segment having an apex;

the distal tip pointing generally toward the proximal portion; and whereby with the catheter inserted into the vasculature, the proximal portion extends from the femoral access site to adjacent the aortic arch of the patient, the first arcuate portion being disposed along the contralateral wall of the ascending aorta, the second arcuate portion spanning the aortic root, the distal tip being engaged in the coronary ostium, the apex being in contact with the contralateral wall of the aorta, the line of action of force tending to displace the distal tip from the ostium being generally coaxial with the second semiaxis, the catheter thus resisting forces tending to displace the distal tip from the ostium.

2. The catheter according to claim 1 wherein the proximal portion and the first arcuate portion lie in the same plane.

3. The catheter according to claim 1 wherein the second arcuate portion lies 5° to 30° out of plane from the first arcuate portion.

4. The catheter according to claim 1 wherein the proximal portion, the first arcuate portion, and the second arcuate portion lie in the same plane.

5. A catheter, adapted for placement within a living anatomy, such as in the human coronary arterial system, the catheter comprising:

a proximal portion, a first arcuate portion, a second arcuate portion, and a distal tip;

the proximal portion being substantially straight;

the first arcuate portion being connected to the proximal portion; the first arcuate portion having a convex curvature, the convex curvature defining a radius of curvature of approximately 3 to 4 inches adjacent to the proximal portion, and blending to a radius of curvature of 1 to 3 inches distally;

the second arcuate portion being connected between the first arcuate portion and the distal tip, the second arcuate portion blending with the first arcuate portion, the second arcuate portion defining two semiaxes, a first semiaxis being adjacent to the distal tip and having a dimension of 1 to 2 cm; a second semiaxis being adjacent to the first arcuate portion and having a dimension of 1 to 3.5 cm, the second arcuate portion defining a segment of a generally ellipsoidal shape, the segment being between 180° and 225°, the segment having an apex; and the distal tip pointing generally toward the proximal portion whereby with the catheter inserted into the vasculature, the proximal portion extends from the femoral access site to adjacent the aortic arch of the patient, the first arcuate portion being disposed along the contralateral wall of the ascending aorta, the second arcuate portion spanning the aortic root, the distal tip being engaged in the coronary ostium, the apex being in contact with the contralateral wall of the aorta, the line of action of force tending to displace the distal tip from the ostium being generally coaxial with the second semiaxis, the catheter thus resisting forces tending to displace the distal tip from the ostium.

6. The catheter according to claim 5 wherein the proximal portion and the first arcuate portion lie in the same plane.

7. The catheter according to claim 5 wherein the second arcuate portion lies 5° to 30° out of plane from the first arcuate portion.

8. The catheter according to claim 5 wherein the proximal portion, the first arcuate portion, and the second arcuate portion lie in the same plane.

* * * * *

UNITED STATES PATENT AND TRADEMARK OFFICE
CERTIFICATE OF CORRECTION

PATENT NO. : 5,603,704
DATED : February 18, 1997
INVENTOR(S) : Brin et al.

It is certified that error appears in the above-identified patent and that said Letters Patent is hereby corrected as shown below:

Col. 1, Line 34: "Burfee" should be "Durfee"

Signed and Sealed this

Thirteenth Day of January, 1998

Attest:

BRUCE LEHMAN

Attesting Officer　　　　Commissioner of Patents and Trademarks